(12) United States Patent
Beadle et al.

(10) Patent No.: US 7,405,329 B2
(45) Date of Patent: Jul. 29, 2008

(54) HYDROFORMYLATION

(75) Inventors: Stephen Wayne Beadle, Prairieville, LA (US); Ronald Dean Garton, Baton Rouge, LA (US); Hubertus Joseph Beckers, Keerbergen (BE); Raphael Frans Caers, Edegem (BE); Arie Van Vliet, Sterrebeek (BE); John J. Houben, Rotterdam (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/582,756

(22) PCT Filed: Dec. 16, 2004

(86) PCT No.: PCT/EP2004/014477

§ 371 (c)(1),
(2), (4) Date: Mar. 23, 2007

(87) PCT Pub. No.: WO2005/058787

PCT Pub. Date: Jun. 30, 2005

(65) Prior Publication Data

US 2007/0282132 A1 Dec. 6, 2007

Related U.S. Application Data

(60) Provisional application No. 60/530,805, filed on Dec. 18, 2003.

(51) Int. Cl.
*C07C 45/50* (2006.01)

(52) U.S. Cl. .................. 568/451; 568/454

(58) Field of Classification Search .......... None
See application file for complete search history.

(56) References Cited

U.S. PATENT DOCUMENTS

| | | | | |
|---|---|---|---|---|
| 2,681,374 A | 6/1954 | Bethea | ............... | 260/683.15 |
| 3,188,351 A | 6/1965 | Lemke | ............... | 260/604 |
| 3,378,590 A | 4/1968 | Usami et al. | ............... | 260/598 |
| 3,864,346 A | 2/1975 | Child et al. | ............... | 260/683.59 |
| 3,868,422 A | 2/1975 | Hart et al. | ............... | 260/604 HF |
| 4,018,846 A | 4/1977 | Mayer | ............... | 260/683.59 |
| 4,049,725 A | 9/1977 | Gueant et al. | ............... | 260/638 B |
| 4,320,237 A | 3/1982 | Kaufhold et al. | ............... | 568/909 |
| 4,334,118 A | 6/1982 | Manning | ............... | 585/529 |
| 4,684,750 A | 8/1987 | Kessen et al. | ............... | 568/883 |
| 5,324,420 A | 6/1994 | De Munck et al. | ............... | 208/124 |
| 5,672,800 A | 9/1997 | Mathys et al. | ............... | 585/520 |
| 5,744,679 A | 4/1998 | Marinangeli et al. | ............... | 585/526 |
| 6,111,159 A | 8/2000 | Huff et al. | ............... | 585/529 |
| 2003/0114718 A1 | 6/2003 | Knoop et al. | ............... | 568/855 |

FOREIGN PATENT DOCUMENTS

| | | |
|---|---|---|
| AU | 200197176 | 6/2002 |
| DE | 100 35 120 | 1/2001 |
| DE | 102 27 995 | 9/2003 |
| EP | 0 188 246 | 7/1986 |
| EP | 0 746 538 | 12/1996 |
| EP | 0 808 298 | 6/1998 |
| GB | 643 503 | 9/1950 |
| GB | 2 142 010 | 1/1985 |
| WO | WO 93/16020 | 8/1993 |
| WO | WO 94/29018 | 12/1994 |
| WO | WO 02/094740 | 11/2002 |

OTHER PUBLICATIONS

Cavani et al., entitled "Effect of Water in the Performance of the Solid Phosphoric Acid Catalyst for Alkylation of Benzene to Cumene and for Oligomerization of Propene" Applied Catalysis A: General, Elsevier Science, , vol. 97, pp. 177-196 (1993), Amsterdam, NL.
"New Syntheses with Carbon Monoxide" by Falbe on p. 17 and 71, New York, 1980.
U.S. Appl. No. 10/582,929, filed Jun. 13, 2006, Beadle et al., Entitled "Improvements in or Relating to Catalysed Reactions".
U.S. Appl. No. 10/582,742, filed Jun. 13, 2006, van Drissche et al., Entitled "Improvements in or Relating to Hydrogenation".

*Primary Examiner*—Sikarl A Witherspoon
(74) *Attorney, Agent, or Firm*—Andrew B. Griffis

(57) ABSTRACT

The gas cycle in a high pressure hydroformylation reaction using a series of at least two reactors is controlled to optimise yield, conversion and selectivity and to control reaction temperature. The control is achieved through balancing fresh gases and recycle gases in each of the reactors and as an optional feature the use of hydrogen off gases from the downstream hydrogenation used in the conversion of the hydroformylation reaction product to product alcohols.

30 Claims, 2 Drawing Sheets

HYDROFORMYLATION

CROSS REFERENCE OF RELATED PATENT APPLICATIONS

This application is a National Stage Application of International Application No. PCT/EP2004/014477, filed 16 Dec. 2004, which claims benefit of U.S. Provisional Application No. 60/530,805, filed 18 Dec. 2003. These applications are incorporated herein by reference.

FIELD OF INVENTION

The present invention relates to improvements in or relating to hydroformylation.

BACKGROUND

Hydroformylation is a well-known process in which an olefin is reacted with carbon monoxide and hydrogen in the presence of a catalyst to form aldehydes and alcohols containing one carbon atom more than the feed olefin. This process has been operated commercially for many years and there have been two principal technology families used. One is known as the low or medium pressure oxo process family and which generally involves the use as catalyst of an organometallic complex of rhodium with organophosphorous ligands for providing the necessary stability at the lower pressures and operates at pressures from 10 to 50 Bar. The second process family is known as the high or medium-pressure process family and generally involves the use of a cobalt or rhodium based catalyst and typically operates at pressures from 50 to 350 Bar. Generally the low pressure processes are used for the hydroformylation of unbranched and terminal, primarily lower olefins such as ethylene, propylene and n-butenes, but also including n-hexene-1, n-octene-1 and mixtures of higher carbon number terminal olefins produced by the Fischer-Tropsch process. The high or medium pressure processes are primarily used for the hydroformylation of linear internal and branched higher olefins such as those containing 5 or more carbon atoms. This process is widely used to produce what are known as "higher alcohols" or aldehydes or acids which are in the $C_6$ to $C_{15}$ range particularly the $C_9$ to $C_{13}$ range. Such materials are typically used in the production of plasticiser or lubricant esters such as the esters of phthalic acid and anhydride, esters of cyclohexane dicarboxylic acids, esters of adipic or trimellitic acid, esters of the various isomers of pyromellitic acid, and polyol esters, but also in surfactant derivatives like ethoxylates, sulfates, or ethoxysulfates.

Hydroformylation is typically performed in large volume reactors which may be continuous or batch reactors. The present invention is concerned with hydroformylation that is performed in a series of at least two reactors.

The present invention is concerned with improving hydroformylation reactions operating continuously and at high or medium pressures and generally using a cobalt based catalyst although other catalyst systems may be used.

As with most large scale industrial chemical processes improvements in the efficiency of the use of raw materials, optimisation of the recycle of unreacted materials and the optimisation of reaction conditions, material balance and other variables are most important. Improvements which can result in a few percentage point increases in conversion, output and efficiency are extremely significant improvements.

High and medium pressure hydroformylation (sometimes known as OXO) reactions involve the reaction of liquid materials with normally gaseous materials which are at least partly dissolved in the liquid during reaction due to the high pressure conditions, and gaseous materials may also be entrained as droplets or bubbles in the liquid phase. Unreacted materials are vented off after the reaction and the present invention is concerned with optimising the reuse of such off-gases in the reaction system. The invention is particularly concerned with the optimisation of gas utilisation by the use of a combination of fresh gaseous feeds and the recycle gases to optimise reaction conditions and thus the conversion and yield of the hydroformylation reaction.

The starting liquids that are involved in high pressure hydroformylation comprise olefins which may be mixtures of olefins such as those obtained from olefin oligomerisation units. For example the olefins may be mixtures of $C_5$ to $C_{12}$ olefins obtained by the phosphoric acid catalysed oligomerisation of $C_3$ and $C_4$ olefins and mixtures thereof, and where olefin mixtures are used, they may have been fractionated to obtain relatively narrow boiling cut mixtures of mostly the appropriate carbon number for the production of aldehydes and alcohols with the desired carbon number. Alternatively the olefins may be obtained by other oligomerisation techniques such as for example the dimerisation of butene using a nickel oxide catalyst, like the Octol® process, or an oligomerisation process for ethylene, propylene and/or butenes using a nickel salt and involving di-alkyl aluminum halides, like the range of Dimersol® processes, or a zeolite catalyst. The olefins may also be obtained from ethylene growth processes, in which case they are often called linear alpha olefins or normal alpha olefins, or they can be mixtures obtained from the Fischer Tropsch process, which primarily contain terminal olefins but which may show some side branches along their longest alkyl chain.

The gases that are involved in high and medium pressure hydroformylation include carbon monoxide and hydrogen, frequently supplied in a mixture that is known as synthesis gas or "syngas". Syngas can be obtained through the use of partial oxidation technology (POX), or steam reforming (SR), or a combination thereof that is often referred to as autothermal reforming (ATR). It can be generated from almost every carbon containing source material, including methane, natural gas, ethane, petroleum condensates like propane and/or butane, naphtha or other light boiling hydrocarbon liquids, gasoline or distillate-like petroleum liquids, but also including heavier oils and byproducts from various processes including hydroformylation, and even from coal and other solid materials like biomass and waste plastics. On liquid feeds, a steam reformer may involve a pre-reformer to convert part of the feed to methane before entering the actual reformer reaction. The gaseous feed streams can also contain inert components such as nitrogen, helium, argon, methane and carbon dioxide which, although mostly inert, are significant in that they have a dilution effect and can help to control reaction temperature. The drawback with these inerts is that their concentrations may change over time, which changes their effects in the hydroformylation step. Nitrogen, helium and argon can come in as impurities with the oxygen supply, or when air or enriched air is used as feed for syngas generation. Also natural gas or methane feeds can contain such inerts. Methane can be left over from incomplete conversion during the syngas generation, or from a methanation reactor that may be included in the flow scheme. As source levels can change, and operating conditions can change, so can the levels of these inerts. Carbon dioxide levels are controlled by reaction conditions in the syngas generation or by absorber and regenerator efficiency if an acid gas absorber/regenerator system is included downstream thereof. Carbon dioxide levels in the fresh syngas are therefore prone to change too.

The gases that are involved in the present invention are fresh gases and the recycle of unreacted gases. An important aspect of the present invention is the use of recycle gases to obtain the appropriate balance of gases in the reactors. Compression of gases, particularly when these need to be brought up to medium and high pressure levels, is energy intensive, and especially inefficient in energy use when the gases comprise significant amounts of hydrogen. Separating unreacted gases from the hydroformylation reaction product, and the partial recycle of this offgas to the reactor, is a well-known way to improve the overall utilisation of the gas feeds to the hydroformylation reactors. It is known that with this gas recycle, due to the presence of inerts in the fresh gases, inerts will build up in the system and reduce the partial pressures of the reactive components like hydrogen and carbon monoxide. Purging a portion of the offgas mixture is the typical solution to avoid excessive buildup of inerts.

Hydroformylation reactions may be continuous or batch reactions and the present invention is concerned with continuous reactions. The reactions with which the invention is concerned take place in a series of two or more reactors and in a preferred embodiment the reactions take place in a series of reactors involving gas lift reactors as lead or front end reactors, more preferably involving loop reactors. The series of reactors may be made up of separate distinct sections within one or a few reaction vessels. Alternatively, one reactor in the series can in itself be made up of different volumes set up in series or in parallel.

The main hydroformylation reaction is the reaction of an olefin with carbon monoxide and hydrogen to produce an aldehyde, Olefin+CO+H$_2$→Aldehyde This reaction consumes equimolar amounts of CO and H$_2$. Its rate of reaction is proportional to the ratio of hydrogen-to-CO. When the fresh feed syngas does not contain CO and hydrogen in equal molar amounts, this H$_2$/CO ratio is bound to change as the reaction progresses through the hydroformylation reactor zone. Also, there are a number of competing and consecutive gas consuming reactions in which the CO and H$_2$ is not necessarily consumed in an equimolar ratio, for example:

Olefin+H$_2$→Paraffin

Olefin+CO+H$_2$O→Acid

Aldehyde+H$_2$→Alcohol

Aldehyde+CO+H$_2$→Formate ester

Aldehydes can condense with alcohols to form a hemi-acetal, R1-CHOH—O—R2, which is not very stable and splits off water to form an unsaturated ether. This again can undergo gas consuming reactions:

Unsaturated ether+H$_2$→di-alkyl ether

Unsaturated ether+CO+H$_2$→ether aldehyde

All these other gas consuming reactions also affect the quantity of CO and hydrogen present throughout each reactor and throughout the series of reactors. Also the rates of these reactions are dependent on conditions and concentrations at each local spot in the reaction zone which are not necessarily constant. The presence of CO and hydrogen is therefore not constant throughout the reaction zone in absolute terms, and even less in relative terms particularly the case when two or more reactors in series are used.

There remains therefore a need to control the concentration and ratio of CO and hydrogen in the second and any subsequent reactors in the ranges desired for that part of the reaction zone. The present invention provides such a control.

In an industrial hydroformylation plant that is producing alcohols, at least part of the product of hydroformylation which consists primarily of aldehydes, or of mixtures of alcohols, aldehydes and formate esters, potentially together with various other compounds, is hydrogenated to convert the aldehydes and formate esters to alcohols and to reduce the level of the impurities. On certain catalysts, these formate esters can, amongst others, split into an alcohol and carbon monoxide, which in the presence of water, can undergo the water-gas-shift reaction and produce hydrogen and carbon dioxide. Alternatively, the formate ester can hydrolyse with water to form the alcohol and formic acid, which then can decompose into carbon monoxide and hydrogen. This formed hydrogen is then available to participate in the hydrogenation reaction. Overall, the hydrogenation reaction is typically operated with a stoichiometric excess of hydrogen, and can therefore result in a stream of unreacted hydrogen. In one aspect, the present invention is therefore also concerned with the use of this stream, to provide the optimum gas balance in the second and subsequent reactors in hydroformylation reactions involving a series of two or more reactors. As with the other streams this hydrogen off gas stream may contain inerts such as nitrogen and methane. It can also contain carbon dioxide as explained earlier. Typically it does however not contain significant amounts of carbon monoxide, because this is against the equilibrium of the water-gas-shift reaction (H$_2$O+CO<--->CO$_2$+H$_2$) that is approached over many catalysts used in the hydrogenation step. Carbon monoxide in the offgas from hydrogenation is typically below 1 mol %, preferably not more than 0.5 mole %, more preferably not more than 0.4 mole %.

It is known, from WO 94/29018, to conduct hydroformylation reactions in a series of reactors and it is also known from WO 94/29018 to feed fresh olefin and fresh synthesis gas to the first and second reactors. This split feed has been found to be beneficial because the first reactor, when it is a gas-lift reactor or preferably a loop reactor, in which the internal fluid circulation and mixing is driven by a density difference provided by having more gas in the upward moving part of the reactor, as compared to the downward moving part, can become unstable as the olefin feed rate, particularly also combined with the additional amount of gas required for the reaction, is increased above a certain threshold. The maximum amount of olefin that can be fed to the lead reactor depends upon many factors, but also on the reactivity of the particular olefin that is being processed. More stable conditions can be realised if the fresh olefin feed is divided between the first and second reactors. It has also been found that if the optimum amount of syngas is fed to the first reactor there can be hydrodynamic instabilities due to the large volumes of gas present. These instabilities can also lead to fluctuations in the temperature in the reactor. This can lead to unique steady state conditions that are periodic, also known as limit cycles. Further increases may enlarge the limit cycle range, and ultimately lead to more severe conditions of a multiplicity, usually a runaway or, at startup, an inability to start the reactor. This situation may be managed by adjusting temperature and catalyst concentration, but it is preferred that a part of the fresh syngas also be fed to the second reactor to alleviate the risk and consequences of the instabilities. Another way to cope with possible instabilities in the lead gas-lift reactor is to provide two lead reactors in parallel, both fed independently and both feeding their product into a third reactor which is in the second position. This method may still be combined with the split feed of olefin and/or fresh syngas to the reactor in second position and in the second reactor for the purposes of this invention. U.S. Pat. No. 4,320,237 also employs a series of reactors.

U.S. Pat. No. 3,378,590 hydroformylates olefins and synthesis gas using a single hydroformylation reactor and cobalt catalysis. Gases that are unreacted during the hydroformylation reaction are recycled to the hydroformylation reactor. In U.S. Pat. No. 3,378,590 the product of hydroformylation containing cobalt carbonyls passes to a hydrogenation zone where the aldehydes are hydrogenated to alcohols and the metal carbonyls are decomposed to the metal and carbon monoxide. The mixture of unreacted hydrogen and the carbon monoxide can be recycled to the hydroformylation reactor.

In U.S. Pat. No. 4,049,725 a mixture of hydrogen and carbon monoxide is used for the hydrogenation of aldehydes and the partially hydrogen depleted waste stream that is obtained after this hydrogenation is used in the hydroformylation reaction.

The ratio of hydrogen to carbon monoxide is an important criterion for the performance of the hydroformylation reaction. As stated by Falbe on page 17 of his book "New Syntheses with Carbon Monoxide", the reaction rate is directly proportional to that ratio. He also states that for each temperature and cobalt concentration, there must be a minimum partial pressure of carbon monoxide present to keep the cobalt-carbonyl catalyst stable, so that plating out of the cobalt as cobalt clusters or as metal does not occur. As a consequence, within these requirements of a minimum carbon monoxide presence, the higher the hydrogen concentration the better.

Hydroformylation reactions typically do not convert all the reactive materials fed to the reactor and so the product of hydroformylation contains unreacted materials particularly carbon monoxide and hydrogen. The traditionally applied excess of carbon monoxide assures the stability of the catalyst even after most of the reaction has taken place. A hydrogen excess is typically desirable to keep the reaction rate up also in the back end of the reactor section.

The products of hydroformylation, predominantly aldehydes and alcohols, but also some formate esters and possibly including heavy materials, are typically fed at least partially, as such or optionally after distillation, to a hydrogenation reactor. This is usually done after catalyst removal, and the products are then hydrogenated to produce alcohols. There is generally an excess of hydrogen in the hydrogenation reactor, which is left over as a waste stream. Optionally, a part of the aldehydes from the hydroformylation reaction may be separated off for use as such or for being converted into carboxylic acids.

There are therefore many gas streams in the commercial manufacture of alcohols and the present invention is concerned with the optimisation of gas utilisation throughout the hydroformylation reaction and also throughout a process involving both hydroformylation and hydrogenation.

DESCRIPTION OF THE FIGURES

The present invention is illustrated by reference to the following drawings in which.

Figure 1:
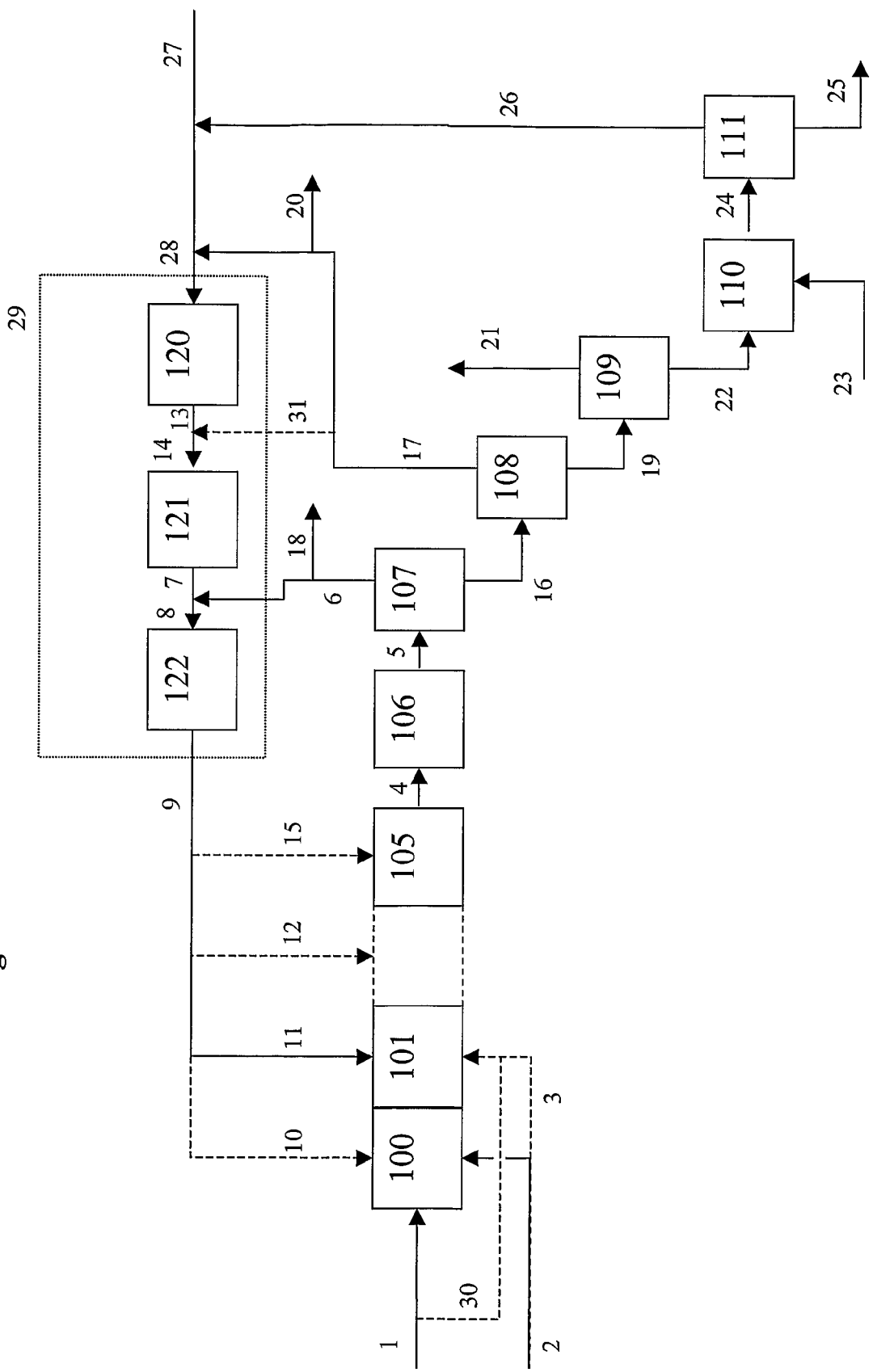
FIG. 1 is a schematic illustration of the overall process for the production of alcohols by hydroformylation according to the present invention. It includes a recycle compressor and also illustrates the source of the hydrogen offgas stream from hydrogenation which may be fed to the recycle compressor.

The present invention is illustrated by reference to FIG. 1 which is a schematic diagram illustrating a hydroformylation facility employing a gas cycle according to the present invention.

DETAILED DESCRIPTION

According to one aspect of the present invention, there is provided a process for the hydroformylation of olefins wherein the hydroformylation takes place in a series of at least two reactors and wherein unreacted gases are recycled to at least the second reactor to adjust the gas composition in the second reactor.

According to a second aspect, the present invention provides a process for the production of alcohols comprising catalytically hydroformylating one or more olefins in a series of at least two reactors to form a hydroformylation product, removing catalyst residues from the hydroformylation product and subsequently hydrogenating the substantially catalyst-free hydroformylation product, wherein unreacted hydrogen from the hydrogenation stage is recycled to at least the reactor in the second position of the series of reactors used in the hydroformylation stage.

According to a third aspect, the present invention provides a process for the production of alcohols comprising catalytically hydroformylating one or more olefins in a series of at least two reactors to form a hydroformylation product, removing catalyst residues from the hydroformylation product to form a substantially catalyst-free hydroformylation product, and subsequently hydrogenating the substantially catalyst-free hydroformylation product, wherein unreacted gases from the hydroformylation reaction are recycled to at least the reactor in the second position of the series of reactors used in the hydroformylation stage and unreacted hydrogen from the hydrogenation stage is recycled to at least the reactor in the second position of the series of reactors used in the hydroformylation stage.

According to a fourth aspect, the present invention provides a high or medium pressure hydroformylation reaction wherein one or more olefins are reacted with carbon monoxide and hydrogen in the presence of a hydroformylation catalyst wherein the hydroformylation is performed in a series of at least two reactors and the feed to the first reactor comprises a mixture of:

i) olefins ii) carbon monoxide iii) hydrogen iv) recycle gases comprising unreacted gaseous materials from the hydroformylation reaction and the feed to the second reactor comprises a mixture of:

i) the reaction product from the first reactor ii) recycle gases comprising unreacted gaseous materials from the hydroformylation reaction.

In a further preferred embodiment the hydroformylation is performed in a series of at least three reactors and the feed to the third reactor comprises:

i) the reaction product from the second reactor ii) recycle gases comprising unreacted gaseous materials from the hydroformylation reaction.

In a further preferred embodiment the hydroformylation is performed in a series of four reactors and the feed to the fourth reactor consists of the reaction product from the third reactor. Additional reactors may be included if desired. Optionally part of the recycle gases and/or a gas rich in hydrogen may also be added to the feed of the fourth and/or subsequent reactors.

The invention further provides apparatus for the operation of the various processes of this invention.

The hydroformylation is typically performed at elevated temperature and pressure in the presence of a hydroformylation catalyst. The optimum temperature and pressure will depend upon the nature of the olefin feed both in terms of the carbon number(s) of the olefins, the structure of the olefin (linear or branched, branch structure, location of the olefinic bond) and the concentration of the olefin in the feed. The feed is typically a mixture of saturated and unsaturated (predominantly olefinic) materials. Typical pressures are from 50 to 350 barg, preferably 150 or 250 to 350 barg, most preferably from 275 to 325 barg. Typical temperatures range from 120 to 185 or 190° C., preferably from 165 or 170 to 180 or 185° C., although certain olefin feeds may preferably be hydroformylated at lower temperatures such as from 100 or 120 to 140° C. for reasons of olefin reactivity or reaction selectivity. The catalyst used in the high pressure hydroformylation is either a rhodium or a cobalt catalyst. Preferably the active cobalt catalyst is hydrocobaltcarbonyl and the rhodium catalyst comprises rhodiumcarbonyls. Using cobalt, typical cobalt concentrations of up to 0.8 wt % cobalt on the olefin content of the feed may be used, preferably from 0.02 or 0.05 wt % to 0.8 wt % cobalt, more preferably from 0.1 wt % to 0.5 wt %. Using rhodium, much lower concentrations may be used, like 0.1 to 200 ppm by weight relative to the olefin feed, preferably 0.2 to 50 ppm, more preferably 0.3 to 20 ppm, even more preferably 0.4 to 5 ppm by weight.

The catalyst may be supplied already absorbed in the olefin feed and/or as fresh catalyst. It is preferably supplied absorbed in the olefin feed. In the case of cobalt, the initial cobalt species can be dicobalt octacarbonyl Co2 (CO)8, or a salt of cobalt with an acid, e.g. cobalt carbonate or a salt of cobalt with another acid of moderate strength, and preferably with an organic acid. Such organic salts may for example be with formic acid or acetic acid, or with higher molecular weight acids like oleic, stearic, or naphthenic acids, or with the heavier carboxylic acids that are made as byproducts in the hydroformylation step or its downstream catalyst removal step and that survive the hydrogenation treatment, eventually ending up in the heavy oxonation fraction byproduct of the aldehyde or alcohol distillation step. The catalyst may also be cobalt oxide or hydroxide. This cobalt source may be preformed in a separate reactor in order to convert it to the carbonyl form, or this conversion may occur in the hydroformylation reactor itself. Under the hydroformylation conditions, an equilibrium is believed to establish itself between two cobaltcarbonyls:

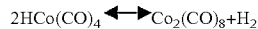

$$2HCo(CO)_4 \leftrightarrow Co_2(CO)_8 + H_2$$

Hydr(id)ocobalt(tetra)carbonyl (HCo(CO)$_4$) is generally believed to be the active catalyst form or at least the precursor to the active catalyst form, which also may be HCo(CO)$_3$. The higher the hydrogen partial pressure in the hydroformylation reaction and the higher the temperature, the greater the concentration of hydrocobalt carbonyl, and hence the greater the reaction rate.

Dicobaltoctacarbonyl, under influence of higher temperature and/or lower partial pressures of carbon monoxide, may split off carbon monoxide and form cobalt cluster forms that gradually contain more cobalt and less carbonyl functions, and which are less and less soluble in the reaction medium, up to the point where the cobalt compounds comes out of solution in forms that contain little carbon monoxide and approach the state of cobalt metal or are metallic. This phenomenon is referred to as "cobalt plating". These clusters and lower carbonyl containing forms of cobalt are inactive for the hydroformylation reaction. It is well known that at a given temperature and cobalt concentration, a certain partial pressure of carbon monoxide is required in order to maintain the stability of the cobaltcarbonyls and to prevent the cobalt to come out of solution and deposit inside the equipment. Consequently, the concentration and the stability of the active hydroformylation catalyst is, under constant operating conditions, affected by the gas composition, e.g. the levels of inerts and those of H$_2$ and carbon monoxide.

The hydroformylation reaction is highly exothermic and the reaction is typically fast. The quantity of heat given off and the rate of heat release to some extent depend upon the nature and structure of the olefin that is being subject to hydroformylation. In general the less branched the olefin and the closer the double bond is towards the end carbon, the more reactive it tends to be. With branched olefins, the reactivity depends on the location of the double bond in relation to the branches. Olefins in which the double bond is located between two branches have, for example, a low reactivity.

The rate of reaction has a substantially exponential relationship to the temperature of the reaction.

It is therefore also important that the conditions of the hydroformylation reaction are controlled to minimize fluctuations in the reaction temperature which can cause variations in the product formed and plating out of cobalt metal from the catalyst. Control is also important for safety purposes to prevent reaction runaway. Accordingly, in addition to optimising gas utilisation, careful management of the gas profile according to the present invention helps to optimise the reaction temperature with the beneficial effects of increasing reaction yield and minimising or eliminating the plating out of the cobalt within the reactor which can occur if the reaction temperature is too high. In this case, extensive cleaning is required with for example nitric acid, requiring that the reactor be taken out of service, or the equipment has to be replaced.

Recycling gas to the reactor in the second position provides a means for providing more free gas and/or more hydrogen to the second and any subsequent reactors, without having to push all that extra gas and/or hydrogen through the reactor or reactors in the lead position, where such extra gas may cause hydraulic or hydrodynamic and temperature instabilities.

Accordingly the present invention provides means for adjusting and controlling the quantity and the composition of the materials fed to the second and any subsequent hydroformylation reactors and thus controlling the gas volumes and compositions and the temperatures that are created in the reactors. The techniques of the invention therefore lead to higher conversion, higher yields, higher selectivity and better operating stability under constant and safe conditions.

In the case of cobalt catalyst, the ratio of hydrogen to carbon monoxide in the fresh syngas is typically about 1.3:1 since at this ratio the plating out of the cobalt is substantially avoided, or sufficiently low to be acceptable. However, due to the reaction in the first reactor where there is some conversion of olefins to aldehydes and alcohols there will be a change in the ratio of hydrogen to carbon monoxide depending on the degree of conversion to alcohol or aldehyde. This is because the conversion to alcohol requires twice as much hydrogen as is used in the formation of an aldehyde. Accordingly, it may be necessary to replenish the hydrogen level in the second and perhaps subsequent reactors (if used) and this can be accomplished according to the present invention by balancing the composition of the recycle gases and/or by introducing unreacted gases from the downstream hydrogenation reactor used to convert aldehydes in the final product of hydroformylation into alcohols. When linear olefins are being processed a lower ratio of hydrogen to carbon monoxide in the first reactor, such as 1:1 or 1.1:1 may be preferred. However, irrespective of the preferred ratio in the feed, it needs to be controlled throughout the hydroformylation reaction section and the present invention provides a convenient technique for its control.

In a preferred embodiment to ensure high olefin conversion the reaction system comprises a series of at least three hydroformylation reactors and, for the same reasons as discussed above in relation to the second reactor, it is preferred that a hydrogen rich gas, composed of optionally fresh syngas and recycle gas from the hydroformylation reaction and/or from the downstream hydrogenation section, is fed to the third reactor together with the reaction product from the second reactor. Although it is within the scope of the present invention we have found that in case of loop reactors of about equal size or volume, there is little benefit in employing a feed of fresh olefin to the third reactor.

In a further preferred embodiment the reactor system includes a fourth reactor in which the final, say up to 5% conversion of the olefins takes place. In this instance we find that it is not always necessary to feed any material to the fourth reactor other than the reaction product of the third reactor, though in certain instances it may still be preferred to add a part of the recycle gases or a hydrogen rich gas also at this stage.

Further embodiments may comprise even more than four reactors in series, for instance six, and those may be set up in stages of 2 reactors in series. Each stage may optionally be provided with liquid product recycle capability, which opens the possibility to cool such recycle and split its injection into the reactors over as many points as desired to keep adequate temperature control. Part of such a stage cooling liquid may even be deviated to an upstream or downstream reactor to assist in temperature control at that point.

The hydroformylation reactors used in the present invention are continuous reactors which are preferably gas-lift reactors like those described in U.S. Pat. No. 3,830,846, U.S. Pat. No. 4,320,237, WO 01/14297, GB 1,308,206 and, more preferably are loop reactors such as those described in U.S. Pat. No. 4,312,837, U.S. Pat. No. 4,379,124, or WO 97/29018. The reactors are provided with cooling coils or jackets for temperature control and it is preferred that the materials be introduced at the bottom of the reactors and are taken off primarily at the top of the reactors, whilst the material not taken off is recycled around the internal or external reactor loop. Accordingly in this invention syngas, olefin potentially containing dissolved or entrained cobalt, potentially water or a hydrocarbon stream containing cobalt, and recycle gas is fed to the bottom of the first reactor, reaction product is taken off at the top of the first reactor and is then fed to the bottom of a second reactor where it is mixed with fresh olefin and fresh syngas. The reaction product is then taken off at the top of the second reactor. In a preferred reaction system the reaction product from the second reactor is fed to the bottom of a third reactor where it is mixed with optionally more fresh syngas and/or recycle gas. This reaction product is then taken off at the top of the third reactor. In a further embodiment the product from the third reactor is then fed to the bottom of a fourth reactor and the final hydroformylation reaction product taken off at the top of the fourth reactor. All reactors in the series can be gas-lift reactors, or loop reactors. If not, only the reactors in the first position and optionally those in second and/or third position may be gas-lift reactors, and the remainder may be vertical tubular reactors as explained above. If a separate water stream is fed to any of the reactors, typically the first of the series, a two-phase water/organic stream may be removed from the bottom of that reactor, and optionally fed through to a point downstream in the flow scheme, preferably a hydroformylation reactor situated downstream, as is illustrated in WO 01/14297.

Many construction materials have been used in fabricating hydroformylation reactors. In particular for the high pressure processes, the strength requirements are demanding. With injection of water into the hydroformylation reaction, also corrosion resistance is required. This has led to reactor designs that couple high strength steels as the main construction material, with an internal lining of a higher quality stainless steel providing corrosion resistance where contact is made with the process medium. Duplex stainless steel, with an austenitic-ferritic microstructure and containing by weight 22-23% Cr, 4.5-6.5% Ni, 3.0-3.5% Mo, 0.14-0.20% N and maximum 0.025% Al is the preferred material of construction for hydroformylation reactors. This duplex stainless steel meets the required corrosion resistance for the process medium with organic acids, carbon monoxide, hydrogen and hydrocarbons at the high pressures. This duplex stainless steel also enables acid cleaning with for instance a mineral acid such as nitric acid to dissolve any cobalt metal that may plate out over time. The yield strength of this construction material is higher, at the design temperature, than that of austenitic stainless steels enabling the wall thickness of the process shell and conditioner tubes to be minimized, thereby improving the heat transfer to the cooling medium in the jacket or in the conditioner shell side. The heat transfer properties of duplex stainless steel are also by themselves better than those of austenitic stainless steels. The duplex stainless steel also has good corrosion resistance towards the cooling water, even if there are chlorides present. Duplex stainless steel is the preferred material also because of the high fatigue endurance limit of this material in the process medium, as compared to austenitic stainless steels.

The control of the temperatures in hydroformylation reaction requires appropriate temperature measurements in the reactors. This is typically done using thermocouples which are provided inside standard thermowells which extend from the reactor wall into the process fluid. In high pressure processes, these standard temperature measurement devices suffer from slow responses due to the higher wall thicknesses required. Therefore the use of flange-ring thermocouples is preferred. Metal sealing rings, such as Destec or Graylock rings, are typically used for sealing the joints between individual pieces of equipment where these are bolted together using flanges. These circular sealing rings may be equipped with a hollow rod crossing the circle of the ring, welded on one side to the ring through which a hole is drilled to provide access for a thermocouple inside the cavity of the rod. On the other side the rod is closed and preferably only supported longitudinally, so that axial displacement is allowed such as because of thermal expansion. Such a hollow rod may have, for example, an external diameter in the range of 4 to 15 mm, and an internal diameter of only 3 to 5 mm. The small wall thickness provides accurate temperature measurement by the thermocouple inside the rod, and fast response of the measurement to temperature changes in the process fluid. Two or more thermocouples may be provided along the length of the rod, either spread along its full length or only half, so that if desired also a radial temperature profile may be measured.

After passing through the series of reactors the final product of the hydroformylation reaction comprises a mixture of alcohols, aldehydes, unreacted olefins, paraffins, formate esters, and heavy oxo fraction, comprising dimer and higher condensation products such as ethers, esters, acetals, hemiacetals, ether aldehydes, ether alcohols, etc. . . . , hydrogen, carbon monoxide, generally catalyst residues and inert materials. The product must then be purified and separated into its components.

The purification involves amongst other steps the removal of dissolved and entrained catalyst species which may be recycled for further use. The reaction product is typically a gas liquid mixture at about 175° C. and 275 bar gauge pressure and due to the high pressure certain normally gaseous materials are dissolved or are entrained in the liquid phase. For cobalt catalysed reactions, the first step in the purification may be the removal of cobalt at high pressure, and the preferred method is by injection of optionally hot and dilute caustic soda and/or sodium carbonate into the reaction product in a decobalter vessel following the final hydroformylation reactor. Preferably in this case, the reaction product from the final reactor is fed to the bottom of the decobalter which is conveniently a long vertical jacketed pipe. In the decobalter the majority of the cobalt is converted into $NaCo(CO)_4$, the water soluble sodium salt of hydrocobaltcarbonyl. If sodium carbonate is used or carbon dioxide is present, a small portion of the cobalt may be converted into solid cobalt carbonate. In absence of carbon dioxide or sodium carbonate, cobalt may be converted to solid cobalt hydroxide, $Co(OH)_2$. We have found that the decobalting is more effective if the caustic soda and/or carbonate and the reaction product from the final hydroformylation reactor are introduced into the decobalter in a manner that avoids intensive mixing of the products—we have found that if the oil phase (reaction product) and the water phase (dilute caustic soda) are brought into contact gradually, less cobalt is lost as cobalt carbonate, because more of it is converted into the water soluble sodium salt. The reaction product of hydroformylation and the dilute base are therefore preferably introduced through separate injection nozzles at least one of which has a tapered opening to allow the material to mix only gradually and with minimal turbulence with the stream of the other material. Minimising the turbulence also minimises the dip in partial pressure of carbon monoxide at the injection point, which minimises the cobalt plating at that point. We have found that the use of a tapered opening, sometimes referred to as a diffuser, for the injection of the reaction product of from 2 to 10° preferably 4 to 8°, most preferably 6° to the nozzle axis is particularly useful.

The decobalter conditions are such that the neutralisation converts the hydrocobalt carbonyl to sodium cobalt carbonyl. In this way the presence of cobalt in the waste water can be avoided. Preferred conditions are to use a stoichiometric excess of sodium hydroxide or carbonate above the amount needed for cobalt neutralisation, an excess of 30 to 200% e.g. 100 to 200% particularly 50 or 100 or 140 to 180% is useful. The decobalter is typically operated at a temperature in the range 125 or 140 to 170° C., preferably 155 to 165° C. It is preferred that sufficient carbon dioxide and/or carbonate is present in the decobalter to buffer the pH of the water separating downstream in the range 7.8 to 8.5. Further possible embodiments can be found in U.S. Pat. No. 5,130,107.

Alternative to this alkaline decobalting method at high pressures, the cobalt may be removed by an acidic and/or oxidative method as described in J. Falbe, in WO 01/14297, in U.S. Pat. No. 4,625,067, U.S. Pat. No. 5,130,107, U.S. Pat. No. 5,235,112, U.S. Pat. No. 5,237,104, U.S. Pat. No. 5,237,105, U.S. Pat. No. 5,321,168, U.S. Pat. No. 5,354,908, U.S. Pat. No. 5,410,090, U.S. Pat. No. 5,457,240, FR 1089983, EP 642488, EP 643683, WO 03/082788 and WO 03/082789. Some of these processes do the catalyst removal from the hydroformylation product at conditions close to the pressures and temperature used in hydroformylation, others may do it at a less severe conditions, being a lower temperature and/or pressure, typically after separating at least a portion of the gases that are contained in the hydroformylation product. The acidic methods typically apply low molecular organic acids, like formic acid and/or acetic acid. They may additionally involve a stripping step, wherein part of the cobalt in a volatile form like $HCo(CO)_4$ is stripped using a gas from the liquid hydroformylation product, and carried into an absorber where it may be absorbed into a suitable liquid like feed olefin or heavy byproducts. The oxidative methods may involve the use of oxygen or an oxygen containing gas, or air. The methods may convert all or only a portion of the cobalt values to their zero valency and/or to their +2 valency equivalents. Part or all of the cobalt values may be converted to cobalt salts, preferably a salt that is soluble in water, more preferably a salt from an organic acid like cobalt formate or acetate. The cobalt values may be fed or recycled to the hydroformylation reaction in a form dissolved in organic liquid such as olefin feed, heavy byproducts or another suitable liquid, in the form of a carbonyl or as a salt, which may be water or oil soluble, and may be formate, acetate, oleate, naphthenate of any other suitable carboxylate dissolved in a suitable organic carrier or in water.

The hydroformylation product, optionally decobalted and combined with the separate water phase formed during decobalting, consists of dissolved gas, entrained gas, water and the hydroformylation product itself. It may be fed, possibly after cooling, to a high pressure separator which separates the free gas from the liquid phase as high pressure offgas. Typically, the high pressure separator operates at a pressure of 250 barg or higher. The preferred pressure is in the range 250 to 300 barg with 260 to 270 barg being most preferred. The gas is separated off and the amount required for recycle is sent to an offgas recycle compressor system. Any excess gas may be disposed of. Such purge may be used to control the recycle gas composition. In addition unwanted gases such as excess nitrogen and other non-condensables may also at least partially be removed to ensure that the recycle of gases according to the present invention does not result in an undesirable build up of inert gases such as nitrogen in the hydroformylation reactors.

The liquid left in the high pressure separator may then be fed, possibly after cooling, to an intermediate pressure separator where the pressure is reduced to a level that a major portion of the gases still dissolved and/or entrained in the liquid from the high pressure separator are released as an intermediate pressure offgas. In certain processes it may be useful to employ more than one high pressure separator in which case two or more intermediate pressure separators may be employed or the liquid products from the high pressure separators may be combined and fed to a single intermediate pressure separator. Here again, any excess gas may be disposed of and unwanted gases such as methane may be removed to ensure that the recycle of gases according to the present invention does not result in an under run of hydrogen and carbon monoxide due to excessive build up of methane or other inerts that are present in the intermediate pressure offgas.

The pressure in the intermediate pressure separator is typically between 50 and 200 barg, preferably between 80 and 120 or 150 barg, more preferably between 90 and 110 barg, and we have found that 100 barg is particularly useful. The reduction in the pressure releases the dissolved gases particularly a part of the unreacted hydrogen and carbon monoxide, and methane, of which a portion can be sent to an offgas recycle compressor system for subsequent recycle. The rest is then typically disposed off as a purge stream. Accordingly offgas from both the high pressure separator and the intermediate pressure separator can be combined in the offgas recycle compressor system to produce the recycle materials employed in the present invention. The flows to the recycle compressor and the purge flows from high and intermediate pressure separators may be used to adjust the balance of the gases, particularly the balance of hydrogen, carbon monoxide, carbon dioxide, nitrogen and methane that are fed to the hydroformylation reactors for the catalysed hydroformylation reaction with the olefin. Where necessary, the hydrogen content may be adjusted by the incorporation of hydrogen from an external source, or by using offgas from the downstream or an associated hydrogenation unit.

The pressure of the liquid or liquids from the intermediate pressure separator may then be further reduced and the liquid or liquids may be routed, possibly after cooling, to a low pressure separator and/or to a washing arrangement, where further catalyst values may be extracted from the hydroformylation product by a water stream. This washing arrangement may be one or a sequence of mixing and separation steps, or may be in the form of a countercurrent or cocurrent extraction tower. This step may benefit from being heated or preheated, partly because this extraction/washing step may be associated with chemical reactions like e.g. disproportionation of $CO_2(CO)_8$ into so-called Co—Co salt ($Co(Co(CO)_4)_2$) and carbon monoxide. We have found that with an alkaline decobalting process, the further reduction of catalyst values is more effective if the level of sodium in such a washing arrangement is kept low.

The offgases for recycle from the high pressure and intermediate pressure separators, and optionally a hydrogen stream from the downstream hydrogenation reactor may be fed to one or a set of recycle compressors and, if necessary fresh hydrogen may be added to produce the recycle stream for hydroformylation having the desired composition. It is preferred that the recycle compressor system comprises a series of gas compressor stages in which the gas pressure is gradually increased to the pressure required in the hydroformylation reaction. We particularly prefer to use a staged recycle compressor system comprising three gas compressors in series, or one compressor having three compression stages. In such a system, the offgas from the high pressure separator from the hydrogenation step and the intermediate pressure separator from the hydroformylation step may be fed to the first compressor stage (which may be the first compressor where three are used) which typically operates at a suction pressure between 40 and 60, e.g. 50 and 60 barg. Hydrogen as the offgas from the downstream hydrogenation reactor (which typically also contains carbon dioxide, carbon monoxide, nitrogen and methane) may also be fed to the first stage (compressor or compressor stage). The gas mixture formed in this first compressor (stage), optionally mixed with gas from the intermediate pressure separator from the hydroformylation step if the pressure thereof is sufficient, may then be fed to a second compressor (stage) where the pressure may be increased, for example, to within the range 140 to 180 barg, preferably 150 to 170 barg. We have found that 160 barg is particularly convenient. The product of the second compressor may then be passed to the third compressor (stage) and additional gas from the high pressure separator may be introduced to ensure the desired composition of the recycle gas feed to the second and optionally other, such as the first, hydroformylation reactors. The pressure is then raised in the third compressor (stage) and the product from the third compressor (stage) fed to the second and first and/or third hydroformylation reactors according to the present invention.

Alternatively, if the downstream hydrogenation process operates at a higher pressure, like 200 barg, the offgas from the hydrogenation unit will also be at a higher pressure, and can be introduced at a point in the recycle gas compression circuit where the pressure is higher, or even directly injected into the preferred points in the hydroformylation process if the hydrogenation pressure is higher than the hydroformylation pressure.

It can be seen therefore that the effective operation of the hydroformylation reaction depends upon optimising the combination of physical conditions such as temperatures, pressures, feed rates of raw materials, space velocities in the reactors and the chemical process conditions. The chemical conditions include in each of the reactors the nature of the olefin feed, relative proportions of olefin feed and other gases including hydrogen, carbon monoxide and inerts such as nitrogen, methane and carbon dioxide as well as catalyst concentration. The amount of offgas that should be recycled and the amount of syngas and olefins that should be fed to the second and, optionally, subsequent reactors depends on many of these variables. However, by establishing the offgas pressure from the high pressure separator and monitoring the composition of the offgas, which includes hydrogen, carbon monoxide and the various inerts, the hydrogen and carbon monoxide partial pressures at the end of the hydroformylation reaction can be calculated and used to control the gas compositions in the upstream hydroformylation reactors. High carbon monoxide partial pressure enhances the stability of the cobalt catalyst and high hydrogen partial pressures assure a favourable hydroformylation reaction rate. These desires are in conflict with the desire for a higher level of inert buildup, which enables more effective gas purging and improved overall gas utilisation, because less valuable hydrogen and carbon monoxide need to be purged with the inerts, but which, within the constraint of a fixed design pressure of the equipment, causes a lower hydrogen and carbon monoxide content of the high pressure off gas and hence also in hydroformylation. The optimal control point therefore is a compromise between these counteracting preferences. Since the consumption of hydrogen in hydroformylation is greater than the consumption of carbon monoxide the present invention can overcome this difficulty by increasing the proportion of hydrogen in the recycle gas that is fed to the second hydroformylation reactor. The options to control the composition of the recycle gas and to divert some of the recycle gas also to the first and/or the third or subsequent reactors further allows to control the gas profile in any of the reactors throughout the reactor train.

As a general guide we have found that the pressure at the end of the hydroformylation reaction should be kept above 170 barg, preferably above 190 or 200 barg, more preferably above 210 or 220 barg, most preferably above 240 barg in order to avoid cobalt plating in the hydroformylation reactors. We have also found that the carbon monoxide content of the offgas from the high pressure separator is desirably such that the partial pressure of CO is above 75 barg, better above 77 barg, preferably above 84 barg since if the partial pressure drops below these levels, cobalt plating can occur in the hydroformylation reactors. Similarly, the hydrogen content of the offgas from the high pressure separator should be such that the partial pressure of hydrogen is desirably above 75 barg, better above 77 barg, preferably above 84, more preferably above 91 barg, since if the partial pressure drops below this level there is a drop in reaction rate. These issues may be controlled by checking the syngas composition, the total pressure and/or the pressure drop across the hydroformylation reaction and the proportion of inerts in the various streams and making the appropriate adjustments. The use of at least two reactors in series and the separate adjustment of the feeds to the reactors by the recycle of gases according to the present invention makes a significant contribution to the efficiency and effective operation of the hydroformylation reaction.

Another important aspect of the hydroformylation reaction is the reaction temperature and temperature control. The reaction is highly exothermic and the temperature generated depends on the reactivity of the olefins and the concentration and ratio of the reactive materials, the catalyst concentration and the volume of inert material present. Accordingly the recycle gases can be used to adjust the amounts and ratios of the reactive materials present and the composition of the recycle gases can be adjusted as a component of reaction temperature control. The reactors are also provided with cooling systems. These can be internal cooling coils or piping, or a jacket around the reactor, or a heat exchanger that is made part of the reactor, as disclosed in WO 01/29018, or a combination thereof. Such a heat exchanger as part of a loop reactor is typically located in the downward leg of the loop, preferably in the lower part of the leg, and is often known as a conditioner. The rate of heat transfer from the reacting fluid to the wall of any of such cooling system, and hence the reactor cooling, is improved when the reacting fluid has a higher velocity relative to the wall of the cooling system. The average temperature and its distribution throughout the reactor, and its control, are therefore also determined by the velocity at which the reaction materials flow within the reactor and the effectiveness of the reactor cooling system. As a minimum, the circulating liquid flow rate inside the reactor should be at least six times larger than the feed rate to the reactor. Preferably the reaction mixture flows at a speed of at least 0.3 meters per second, more preferably of from 0.5 to 2.0 meters per second, most preferably of from 0.8 to 1.2 m/s, although it needs to be understood that the upward part may have a different cross-section from the downward part, and the velocities may be thus be different in the different reactor sections.

In the preferred use of gas lift reactors the circulation in the reactor is important for the control of the degree of mixing of the reactants and for an even temperature distribution. In such reactors the liquid circulation is primarily driven by a density difference between the upward moving fluid and the downward moving fluid. This density difference is caused by a difference in the presence of free gas between the rising and the downcoming liquid. We have found that in order to obtain a well mixed reaction mixture in a loop reactor that is in the lead position of a reactor train, the rate of circulation within the loop should be at least six times the rate of feed of materials to the reactor, we have also found that a temperature difference between the reactor outlet temperature and the conditioner inlet temperature of greater than 20° C. can indicate insufficient circulation. Preferably this temperature difference is lower than 20° C., such as not more than 16 or even 10° C., preferably not more than 5° C., however the preferred difference depends on the reactivity of the olefins being hydroformylated and on the other operating conditions.

Cooling water or another medium such as an alkanol, for example methanol, is provided to the cooling system provided, if present, as part of each reactor. Particularly the early reactors in a reactor train may be provided with a cooling system. Such cooling system may comprise a jacket and a conditioner, for each reactor. The flow rate of the cooling water or medium is preferably substantially constant and high, in order to enhance heat transfer, so the cooling system may comprise a pump around setup for circulation over the jacket and/or the conditioner. In a loop reactor, the cooling water circulation is preferably in countercurrent with the process fluid flow. Hot water liquid or vapour may be removed from this system and colder water may be introduced into it. The colder water flow rate will be selected according to the size of the reactor and the calculated heat generated by the reactor. For reactions to be performed in the temperature range of 170° C. to 190° C. we prefer that the cooling water has a temperature in the range of 140-170° C., and the colder water introduced may have a temperature of 90 or 100 to 125° C. If the feed olefin is low in reactivity, for instance because it is of a high carbon number, the cooling system may be utilised to supply heat into the reacting fluid.

In order to improve the selectivity of the hydroformylation reaction, water may be injected into the hydroformylation reactors. We have found that the injection of water reduces the formation of formate esters and heavy by-products. When used, water should be injected into the first reactor and may also be injected into the second and subsequent reactors that are used but we have found that this is not always essential. In a gas-lift reactor, the formation of a significant volume of a stagnant free water phase in the bottom can become an impediment or even an obstruction to the circulation of the reactor fluid. Gas-lift reactors from which any free water is continuously removed from the bottom have been described in WO 01/14297. If there is no water removal capability, the quantity of water that is introduced should preferably not exceed or not exceed by more than 10 or 20% the solubility of the water in the reaction mixture, this to avoid the formation of a stagnant free water phase in the reactor. Some water above the solubility limit may be allowed, as long as fluid flows are sufficient to keep the water in a dispersed form and circulating. The solubility of water in the reaction mixture depends upon the composition and the temperature of the reaction mixture. We have found that no more than 2 wt % of water based on the weight of olefin feed should be used in the first reactor and typically from 1.0 wt % to 1.75 wt % particularly 1.5 wt % should be used. The weight of the olefin feed is the weight of unsaturated materials in the feed which is typically above 95 wt % of the feed and frequently about 99 wt % of the feed. If the volume of the lead reactor is relatively small, and the olefin conversion reached at its outlet is limited, the preferred level of water in its feed may be even lower, such as about 0.6 wt %. Where water is injected into the second reactor, similar considerations may apply depending on the design of the reactor. Due to the different liquid composition in the second reactor, the water solubility may be different in this reactor, and we prefer to use typically a total of 2.5 wt % water present based on the olefin feed. It needs to be understood that these water levels depend on the olefin type and alcohol product that is processed, due to the different water solubility of the corresponding process streams. It also needs to be understood that the distribution of the water injected depends on the size of the individual reactor stages.

We have found that the injection of water provides a significant improvement in olefin utilisation as well as carbon monoxide utilisation per unit of alcohol produced. The water should be injected into a reactor in a manner that ensures good mixing of the water with the reactants and also prevents large fluctuations in the olefin to water feed ratios.

Accordingly it is preferred that the water be injected into a full operational reactor and when a loop reactor is used it is preferred that the materials are circulating at a velocity of at least 0.6 meters/sec when the water is injected. It is also preferred that the water and the olefin are continuously introduced into the reactor at the desired water to olefin ratio. Given the range of variables that must be integrated and optimised to optimise the effectiveness of the hydroformylation reaction, the following table is provided as a guide to the conditions which may be employed. The table is however not to be considered as limiting the scope of the present invention.

passes to the second hydroformylation reactor (101) into which fresh synthesis gas (3) may, if desired, be injected. Also some of the feed olefins (30) may be bypassing the first reactor. The product of reactor (101) may then pass to subsequent reactors (up to (105)) if they are employed. The final product of hydroformylation (4) then passes to the cooling exchanger (106) and the cooled product (5) passes to the high pressure separator (107) where it is split into unreacted gas-

| Process Variable | Min | Normal | Max | Unit |
| --- | --- | --- | --- | --- |
| Number of reactors per train | 3 | 4 | | two parallel trains |
| Feed Rate of Octenes to Oxo | | | 30.0 | t/hr |
| | | | | for the two trains |
| Clean Olefin Bypass to 2$^{nd}$ reactor | 0.0 | 1.6 | 2.4 | t/hr/train |
| Total Syngas Feed Rate to Oxo | | | 15200 | Nm$^3$/hr |
| Syngas Bypass to 2$^{nd}$ reactor | 0.0 | 1400 | 2000 | Nm$^3$/hr/train |
| Syngas H$_2$/CO ratio | 1.25 | 1.31 | 1.40 | (mol/mol) |
| Total Offgas Recycle to Oxo | | | 3500 | Nm$^3$/hr |
| Into the second reactor | | | | For the two trains |
| Oxo Water Injection | | | | |
| 1$^{st}$ reactor | | | 1.5 | wt % on olefin feed to the 1$^{st}$ reactor |
| 1$^{st}$ and 2$^{nd}$ reactor together | | | 2.5 | Wt % on olefin feed to the reactor train |
| Cobalt concentration | 0.25 | 0.35 | 0.45 | wt % on total Oxo olefin feed |
| Cobalt to Oxo | 60 | 100 | 140 | kg Co/hr |
| Oxo Reactor Temperature | | | | |
| Outlet 1$^{st}$ reactor | 150 | 167 | 175 | ° C. |
| Outlet 2$^{nd}$ to 4$^{th}$ | 165 | 175 | 180 | ° C. |
| ΔT outlet lead reactor/conditioner inlet | 3 | 10 | 20 | ° C. |
| Oxo Reactor Pres. | | | | |
| Oxo inlet | 270 | 290 | 310 | barg |
| HP separator | 240 | 255 | 260 | barg |
| ΔP | 25 | 35 | 70 | barg |
| Oxo HP Offgas Rate | 600 | 1000 | 1500 | Nm$^3$/hr/train |
| Oxo HP Offgas Composition | | | | |
| H$_2$ | 30 | 34 | 38 | vol % |
| CO | 32 | 35 | 40 | vol % |
| Decobalter Outlet Temperature | 150 | 165 | 175 | ° C. |
| Caustic Feed Temperature | 75 | 80 | 85 | ° C. |
| Caustic Feed Rate | 1500 | 2200 | 3000 | kg/hr/train |
| NaOH concentration in Caustic Feed | 2.0 | 4.0 | 5.0 | wt % |
| 50 wt % NaOH Feed from tankage | 175 | 350 | 500 | kg/hr |
| Oxo water circulation per reactor | 200 | 240 | 250 | m$^3$/hr |
| Oxo cold water supply flow | 140 | 147 | 150 | m$^3$/hr |
| Oxo cold water supply pressure | 13 | 14 | 15 | barg |
| Oxo cold water temperature | 90 | 115 | 125 | ° C. |

FIG. 1 shows a series of hydroformylation reactors comprising a first reactor (100), a second reactor (101) and optionally subsequent reactors (up to 105). Following hydroformylation the product is cooled in heat exchanger (106) and then passes to a high pressure separator (107), then to an intermediate pressure separator (108) and to a low pressure separator (109) and the depressurised hydroformylation product is then passed to a hydrogenator (110) from which the hydrogenated product passes to another high pressure separator (111). Not shown in this flow scheme are the steps associated with the removal of the catalyst and/or water from the hydroformylation reaction product. The process steps (120), (121) and (122) are all compressors and together make up the recycle gas compressor system.

Accordingly, olefins (1) and synthesis gas (2) are fed to the first hydroformylation reactor (100) and the product then eous material (6) (where most of the unreacted hydrogen is retrieved) and liquid or liquids. The separated liquid or liquids (16) then pass to the intermediate pressure separator (108) where they are split into more unreacted gaseous material (17), containing a significant portion of the unreacted carbon monoxide, and the liquid material (19) which then passes to the low pressure separator (109), which separates off a low pressure offgas (21). The liquid hydroformylation product (22) then passes to the hydrogenation reactor section (110), to which is fed hydrogen (23) for the catalytic hydrogenation of the material (22). After hydrogenation (which may also be in a series of reactors) the hydrogenated material (24) passes to another high pressure separator where unreacted hydrogen (26) is taken off from the hydrogenated product (25).

The gaseous materials (6); (17) and the hydrogen (26) may then all be used in the gas recycle to control and adjust the gases present in the hydroformylation reactors that are located in the second and subsequent positions. The hydrogen (26) may, if desired be combined with a fresh hydrogen (27) from another source, and fed to the first stage compressor in the recycle gas compressor system (29). Optionally, some or all of the offgas (17) from the intermediate pressure separator may be combined with this hydrogen rich mixture. The stream (13) from the first stage compressor, if pressure levels permit, can be combined with some or all (31) of the offgas from the intermediate pressure separator to produce the stream (14) that is fed to the second stage compressor (121). The line carrying the stream (17) is preferably provided with a purge means (20) to enable inert materials and any other excess unwanted gases to be removed.

Similarly, the gaseous stream (6) is fed to and combined with the stream (7) exiting the second stage compressor (121) to produce the stream (8) that is fed to the third stage compressor (122). The line carrying the stream (6) is preferably provided with a purge means (18) to enable inert materials and any other excess unwanted gases to be removed.

The stream (9) exiting the recycle gas compressor system is then fed (see (11)) to the second hydroformylation reactor (101) to optimise the gas content and composition in that reactor. As shown, parts of the recycle stream (9) may, if desired, also be fed to the other hydroformylation reactors.

Figure 2:
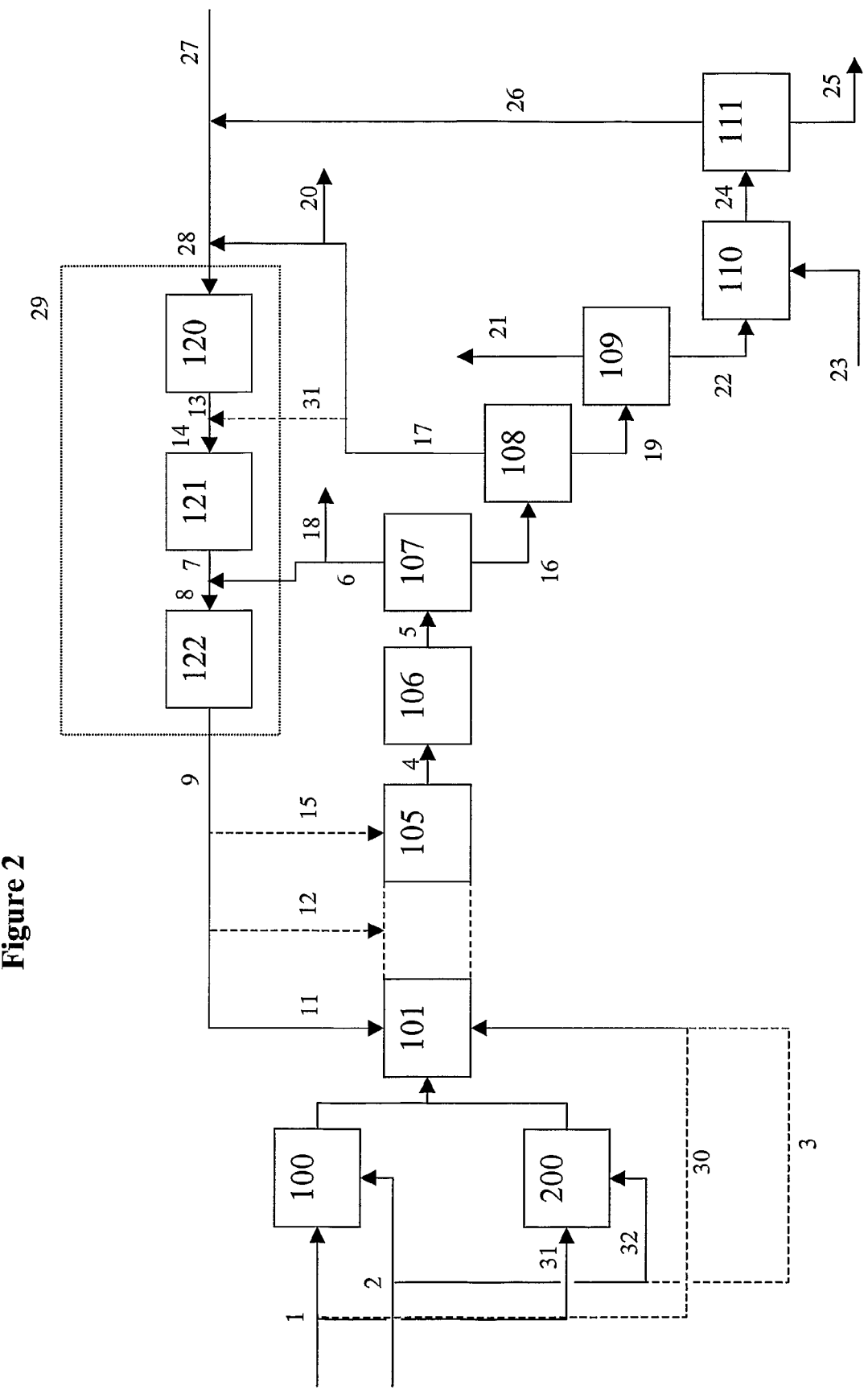
FIG. 2 is an alternative embodiment to the overall process shown in FIG. 1.

In FIG. 2, the front end of the hydroformylation reactor series is split such that two reactors (100, 200) are provided in the lead position, and individually fed with olefin feed (1, 31) and with synthesis gas (2, 32). The products of these two lead reactors are then combined and passed on to the reactor (101) that is in the second position. Optionally, a portion of the olefin feed (30) and/or of the synthesis gas (3) are also passed on to this reactor. The rest of the flow diagram of FIG. 2 is the same as the equivalent parts of FIG. 1. Not shown on FIG. 2 is the possibility to have a portion of the recycle gas (9) passed on to one or all of the reactors that are in the lead position (100, 200).

The front end of the hydroformylation reactor series may be split further into more than 2 lead reactors, optionally with more than one reactor being in the second position, at least one of which receives a portion of the recycled gas (9). These variations are considered further alternate embodiments of the present invention.

The invention claimed is:

1. A process comprising:
    hydroformylating at least one olefin with carbon monoxide and hydrogen in the presence of a hydroformylation catalyst to form a hydroformylation product, wherein the hydroformylation takes place in a series of at least two hydroformylation reactors;
    recycling unreacted gases to at least the hydroformylation reactor in the second position, wherein the unreacted gases originate from the hydroformylation step or from a subsequent hydrogenation step;
    passing the hydroformylation product to a high pressure separator and separating an offgas having a concentration of carbon monoxide such that the partial pressure of carbon monoxide in the offgas is above 75 barg.

2. The process according to claim 1 comprising
    removing catalyst residues from the hydroformylation product to form a substantially catalyst-free hydroformylation product, and
    subsequently hydrogenating the substantially catalyst-free hydroformylation product, wherein the unreacted gases passed to at least the hydroformylation reactor in the second position comprise unreacted hydrogen from the hydrogenation step.

3. The process according to claim 2 wherein the unreacted gases that are recycled comprise unreacted gases from the hydroformylation step and unreacted hydrogen from the hydrogenation step.

4. The process according to claim 1 wherein the hydroformylation process is selected from the group consisting of a high pressure hydroformylation process and a medium pressure hydroformylation process, wherein feed to the first hydroformylation reactor; comprises a mixture of:
    i. one or more olefins;
    ii. carbon monoxide;
    iii. hydrogen; and
    iv. recycle gases comprising unreacted gas from the one more hydroformylation reactors;
and the feed to the hydroformylation reactor in the second position comprises a mixture of the reaction product from the first reactor and recycle gases comprising unreacted gas from one or more of the hydroformylation reactors.

5. The process according to claim 4 comprising hydroformylating the olefin(s) in a series of at least three reactors and the feed to the reactor in the third position comprises the reaction product from the reactor in the second position and recycle gases from one or more of the hydroformylation reaction.

6. The process according to claim 4 comprising hydroformylating the olefin(s) in a series of four reactors and the feed to the reactor in the fourth position consists of the reaction product from the reactor in the third position.

7. The process according to claim 1 comprising hydroformulating the olefin(s) at a pressure of from 50 to 350 barg.

8. The process according to claim 1 comprising hydroformylating the olefin(s) at a temperature of from 120 to 185° C.

9. The process according to claim 1 wherein the hydroformylation catalyst is absorbed in the olefin feed.

10. The process according to claim 1 wherein the hydroformylation catalyst comprises a rhodium catalyst or cobalt catalyst.

11. The process according to claim 10 wherein the catalyst is a cobalt catalyst and the molar ratio of hydrogen to carbon monoxide used for hydroformylation is about 1.3:1.

12. The process according to claim 10 wherein the catalyst is a cobalt catalyst and wherein the process further comprises contacting sodium hydroxide soda or sodium carbonate with the hydroformylation reaction product in a decobalter vessel.

13. The process according to claim 12 comprising contacting a stoichiometric excess of 100 to 200% of sodium hydroxide soda or sodium carbonate with the hydroformylation product.

14. The process according to claim 12 wherein the decobalter vessel is operated at a temperature in the range 155-165° C.

15. The process according to claim 10 wherein the catalyst is a cobalt catalyst and the process further comprises removing the cobalt catalyst from the hydroformulation reaction product by contacting the hydroformylation reaction product with an acid and/or an oxidant.

16. The process according to claim 15 wherein the acid comprises formic acid or acetic acid.

17. The process according to claim 15 wherein the oxidant comprises at least one species selected from the group consisting of oxygen, an oxygen containing gas, and air.

18. The process according to claim 1 wherein the partial pressure of carbon monoxide is above 77 barg.

19. The process according to claim 18 wherein the high pressure separator operates at a pressure of at least 250 barg.

20. The process according to claim 18 comprising passing at least a portion of the offgas from the high pressure separator to an offgas recycle compressor system.

21. The process according to claim 18 comprising feeding the liquid left in the high pressure separator to an intermediate pressure separator and reducing the pressure to a level at which gases entrained with the liquid from the high pressure separator are released as an intermediate pressure offgas.

22. The process according to claim 21 wherein the pressure in the intermediate pressure separator is between 80 and 120 barg.

23. The process according to claim 21 wherein at least a portion of the intermediate pressure offgas is sent to an offgas recycle compressor system for subsequent recycle.

24. The process according to claim 1 wherein the recycling step employs a compressor system comprising a series of gas compressor stages.

25. The process according to claim 24 wherein the recycle compressor system comprises three gas compressor stages in series.

26. The process according to claim 25 comprising feeding high pressure offgas and intermediate pressure offgas from the hydroformylation step (and optionally unreacted gas from the hydrogenation stage) to the first compressor stage, which operates at a suction pressure between 50 and 60 barg.

27. The process according to claim 26 comprising feeding the gas mixture discharged from the first compressor stage, optionally with intermediate pressure offgas, to the second compressor stage and increasing the pressure to within the range of 140 to 180 barg.

28. The process according to claim 27 comprising feeding the gas mixture discharged from the second compressor stage, optionally with high pressure offgas, to the third compressor stage.

29. The process according to claim 1 wherein the hydroformylation reactors and any further processing equipment in contact with the hydroformylation product are constructed from duplex stainless steel.

30. The process according to claim 4, wherein the feed to the hydroformylation reactor in the second position further comprises fresh olefin and fresh syngas.

* * * * *